US009381348B2

(12) United States Patent
Romero et al.

(10) Patent No.: US 9,381,348 B2
(45) Date of Patent: *Jul. 5, 2016

(54) LEADS WITH SEGMENTED ELECTRODES AND METHODS OF MAKING AND USING THE LEADS

(71) Applicant: BOSTON SCIENTIFIC NEUROMODULATION CORPORATION, Valencia, CA (US)

(72) Inventors: Daniel James Romero, Granada Hills, CA (US); Joshua Dale Howard, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 14/286,889

(22) Filed: May 23, 2014

(65) Prior Publication Data

US 2014/0358209 A1    Dec. 4, 2014

Related U.S. Application Data

(60) Provisional application No. 61/829,918, filed on May 31, 2013.

(51) Int. Cl.
*A61N 1/05* (2006.01)
*A61N 1/36* (2006.01)

(52) U.S. Cl.
CPC ............ *A61N 1/0551* (2013.01); *A61N 1/0534* (2013.01); *A61N 1/3605* (2013.01); *Y10T 29/49208* (2015.01)

(58) Field of Classification Search
CPC . A61N 1/0551; A61N 1/0534; A61N 1/3605; Y10T 29/49208

USPC .............................................. 607/116; 29/876
See application file for complete search history.

(56) References Cited

U.S. PATENT DOCUMENTS 4,602,624 A    7/1986  Naples et al.
4,630,611 A   12/1986  King
(Continued)

FOREIGN PATENT DOCUMENTS

EP    0580928 A1    2/1994
EP    0650694 B1    7/1998
(Continued)

OTHER PUBLICATIONS

U.S. Appl. No. 14/469,214, filed Aug. 26, 2014.
(Continued)

*Primary Examiner* — Alyssa M Alter
(74) *Attorney, Agent, or Firm* — Lowe Graham Jones PLLC; Bruce E. Black

(57) ABSTRACT

A stimulation lead includes a lead body. Terminals and electrodes are disposed along opposing end portions of the lead body and are electrically-coupled to one another via conductors. The electrodes include segmented electrodes. Each of the segmented electrodes includes a proximal end, a distal end, an exterior surface, an interior surface opposite the exterior surface, a first side-wall extending radially between the interior surface and the exterior surface from the distal end to the proximal end, and a second side-wall opposite to the first side-wall and extending radially between the interior surface and the exterior surface from the distal end to the proximal end. At least one of the segmented electrodes defines an open cavity that is formed along the first side-wall of the segmented electrode and that facilitates adhesion of the segmented electrode to the lead body.

20 Claims, 10 Drawing Sheets

(56) References Cited

U.S. PATENT DOCUMENTS

| | | |
|---|---|---|
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,391,985 B2 | 3/2013 | McDonald |
| 8,583,237 B2 | 11/2013 | Bedenbaugh |
| 8,649,873 B2 | 2/2014 | Moffitt et al. |
| 9,149,630 B2 * | 10/2015 | Howard ............... A61N 1/0534 |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0054941 A1 | 2/2009 | Eggen et al. |
| 2009/0204192 A1 | 8/2009 | Carlton et al. |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0039590 A1 | 2/2014 | Moffitt et al. |
| 2014/0088666 A1 | 3/2014 | Goetz et al. |
| 2014/0123484 A1 | 5/2014 | DiGiore et al. |
| 2014/0142671 A1 | 5/2014 | Moffitt et al. |
| 2014/0155971 A1 | 6/2014 | Pianca et al. |
| 2014/0180375 A1 | 6/2014 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2008/100841 A1 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

U.S. Appl. No. 14/557,211, filed Dec. 1, 2014.
International Search Report and Written Opinion for PCT Application No. PCT/US2014/039433 mailed Oct. 15, 2014.
U.S. Appl. No. 14/286,940, filed May 23, 2014.
U.S. Appl. No. 14/286,934, filed May 23, 2014.
U.S. Appl. No. 14/286,829, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,797, filed May 23, 2014.

* cited by examiner

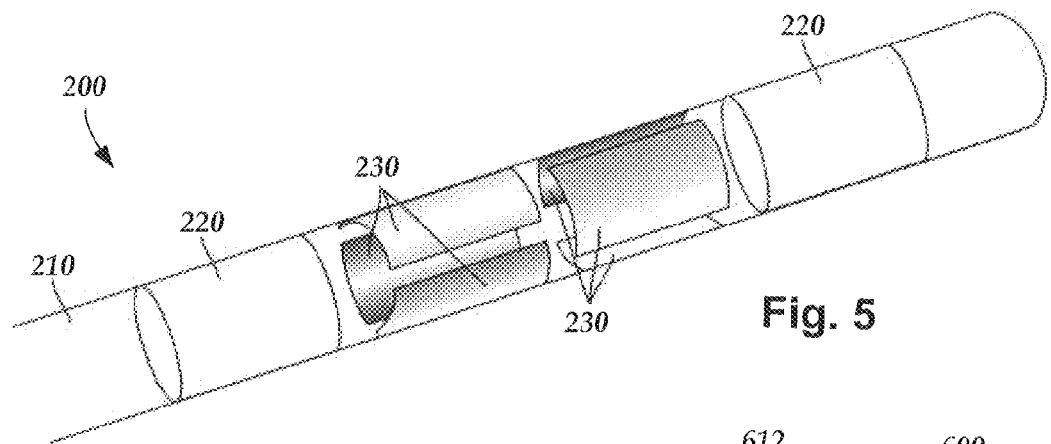
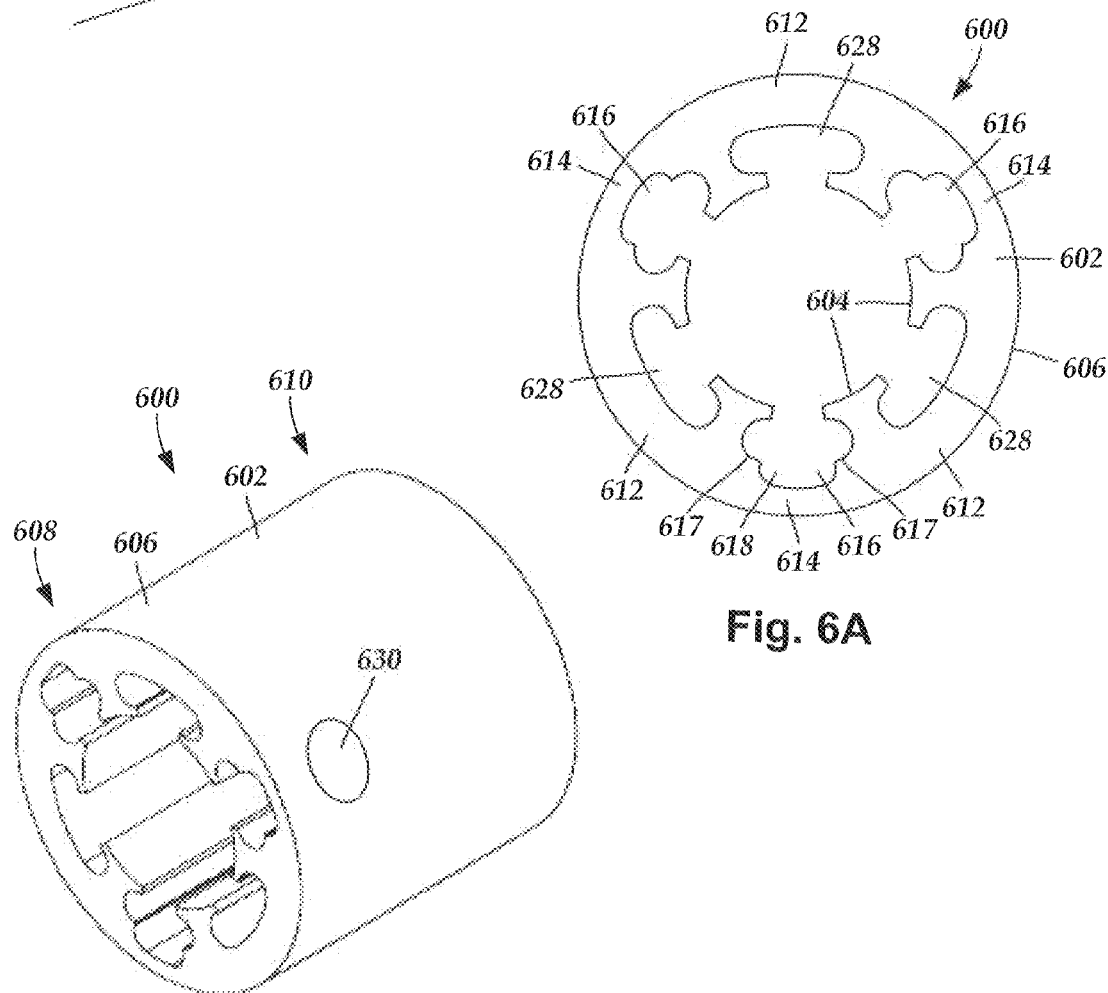

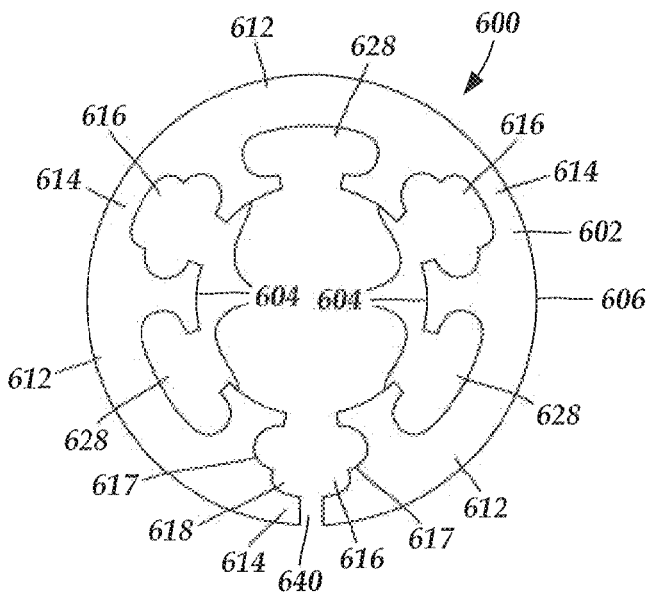
Fig. 6C
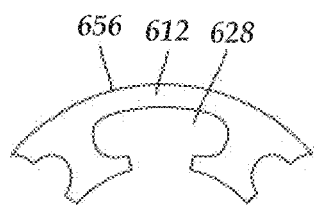
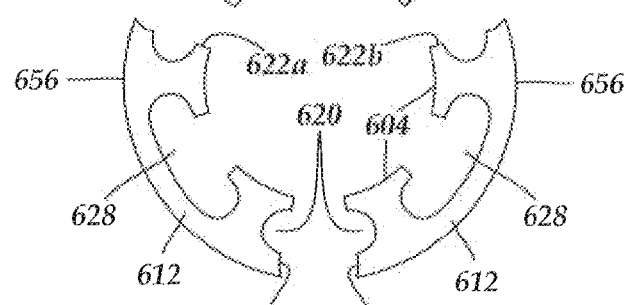
Fig. 6D
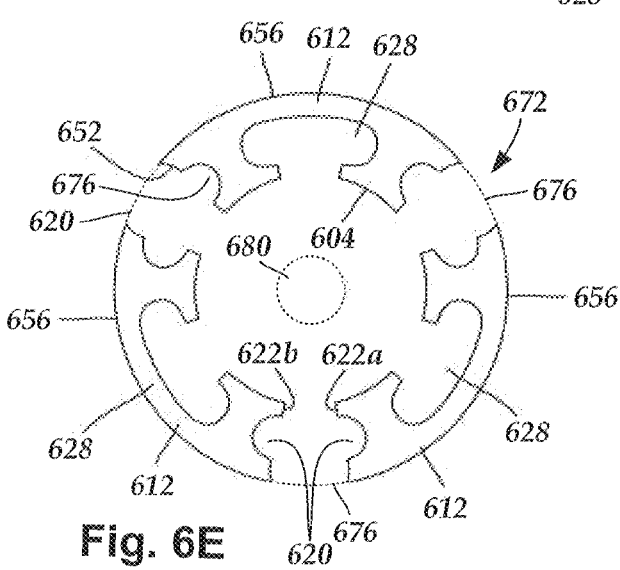
Fig. 6E

LEADS WITH SEGMENTED ELECTRODES AND METHODS OF MAKING AND USING THE LEADS

This application claims the benefit under 35 U.S.C. §119 (e) of U.S. Provisional Patent Application Ser. No. 61/829,918, filed May 31, 2013, which is incorporated herein by reference.

FIELD

The invention is directed to the area of electrical stimulation systems and leads and methods of making and using the systems and leads. The present invention is also directed to electrical stimulation leads with segmented electrodes having internal lead-retention features, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

In one embodiment, a stimulation lead includes a lead body having a longitudinal surface, a distal end portion, a proximal end portion, and a longitudinal length. Terminals are disposed along the proximal end portion of the lead body. Electrodes are disposed along the distal end portion of the lead body. Conductors electrically couple the terminals to the electrodes. The electrodes include segmented electrodes. Each of the segmented electrodes includes a proximal end, a distal end, an exterior surface, an interior surface opposite the exterior surface, a first side-wall extending radially between the interior surface and the exterior surface from the distal end to the proximal end, and a second side-wall opposite to the first side-wall and extending radially between inferior surface and the exterior surface from the distal end to the proximal end. At least one of the segmented electrodes defines at least one open cavity formed along the first side-wall of the segmented electrode and extending circumferentially inwardly and extending from the distal end to the proximal end. The at least one open cavity is configured and arranged to facilitate adhesion of the segmented electrode to the lead body.

In another embodiment, a method of making a stimulation lead includes disposing at least one pre-electrode along a distal end portion of a lead body. The at least one pre-electrode includes a substantially-cylindrical body having an outer surface, an interior surface opposite the outer surface, a proximal end, and a distal end. The body includes a plurality of segmented electrodes disposed along the body in a spaced-apart configuration. Each of the plurality of segmented electrodes extends between the proximal end and the distal end of the body. Each of the plurality of segmented electrodes also extends between the interior surface of the body and an exterior surface. Each of the plurality of segmented electrodes includes a first side-wall and a second side-wall opposite to the first side-wall. The first side-wall and the second side-wall each extend radially between the interior surface and the exterior surface from the distal end to the proximal end. The plurality of segmented electrodes includes a first segmented electrode and a second segmented electrode. The first segmented electrode defines a first open cavity extending circumferentially inwardly into the first side-wall from the distal end to the proximal end. Connecting material couples the first segmented electrode to the second segmented electrode. A cutout is defined along the body between the first segmented electrode and the second electrode. Non-conductive material is placed within the first open cavity to facilitate retention of the segmented electrode with the lead body.

In yet another embodiment, a pre-electrode for a stimulation lead includes a substantially-cylindrical body having an outer surface, an interior surface opposite the outer surface, a proximal end, and a distal end. A plurality of segmented electrodes is disposed along the body in a spaced-apart configuration. Each of the plurality of segmented electrodes has opposing side-walls extending radially between the proximal end and the distal end of the body. At least one open cavity is defined along at least one side-wall of at least one of the plurality of segmented electrodes. The at least one cavity extends between the proximal end and the distal end of the body. Connecting material is disposed along the outer surface of the body. The connecting material couples each of the plurality of segmented electrodes to one another. A plurality of cutouts is defined between adjacent segmented electrodes of the plurality of segmented electrodes. At least one alignment feature forms an opening extending between the outer surface of the body and one of the plurality of cutouts.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5 is a schematic perspective view of another embodiment of a portion of a lead having a plurality of segmented electrodes arranged in a staggered orientation, according to the invention;

FIG. 6A is a schematic transverse cross-sectional view of one embodiment of a pre-electrode having oval-shaped channels and cutouts with side open cavities, according to the invention;

FIG. 6B is a schematic perspective view of one embodiment of the pre-electrode of FIG. 6A, according to the invention;

FIG. 6C is a schematic transverse cross-sectional view of one embodiment of the pre-electrode of FIG. 6A with an alignment slit defined along a cutout of the pre-electrode, according to the invention;

FIG. 6D is a schematic transverse cross-sectional view of one embodiment of a set of segmented electrodes formed by removing connecting material of the pre-electrode of FIG. 6A or FIG. 6C, according to the invention;

FIG. 6E is a schematic transverse cross-sectional view of one embodiment of the set of segmented electrodes of FIG. 6D disposed along a lead body, according to the invention;

DETAILED DESCRIPTION

The invention is directed to the area of electrical stimulation systems and leads and methods of making and using the systems and leads. The present invention is also directed to electrical stimulation leads with segmented electrodes having internal lead-retention features, as well as methods of making and using the segmented electrodes, leads, and electrical stimulation systems.

A lead for deep brain stimulation may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

In at least some embodiments, a practitioner may determine the position of the target neurons using recording electrode(s) and then, position the stimulation electrode(s) accordingly. In some embodiments, the same electrodes can be used for both recording and stimulation. In some embodiments, separate leads can be used; one with recording electrodes which identify target neurons, and a second lead with stimulation electrodes drat replaces the first after target neuron identification. In some embodiments, the same lead may include both recording electrodes and stimulation electrodes or electrodes may be used for both recording and stimulation.

Figure 1:
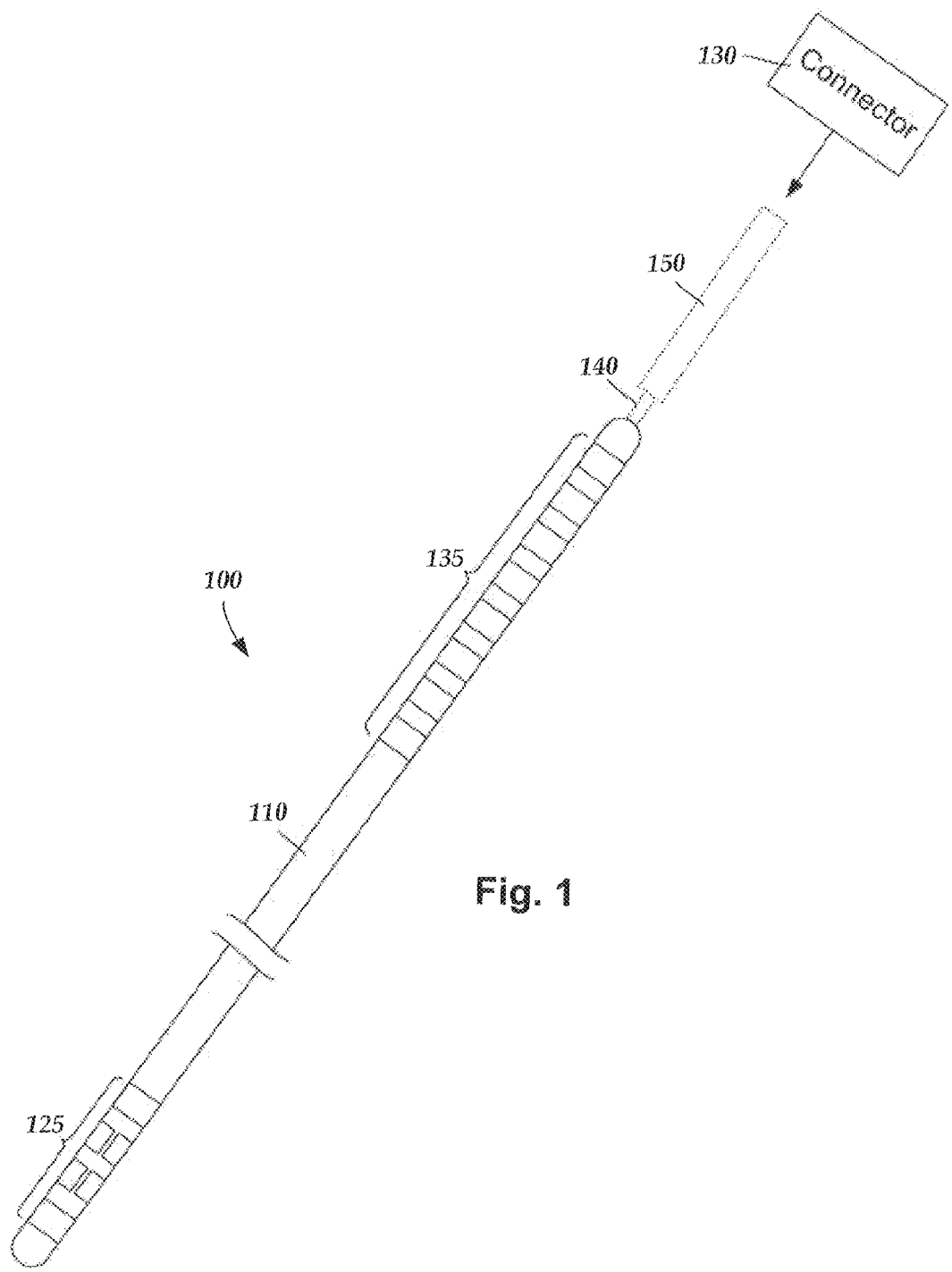
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 130 for connection of the electrodes to a control unit, and a stylet 140 for assisting in insertion and positioning of the lead in the patient's brain. The stylet 140 cast be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 130 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more or fewer than eight stimulation channels (e.g., 4-, 6-, 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to farther identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes, however, typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to mote precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

Figure 2:
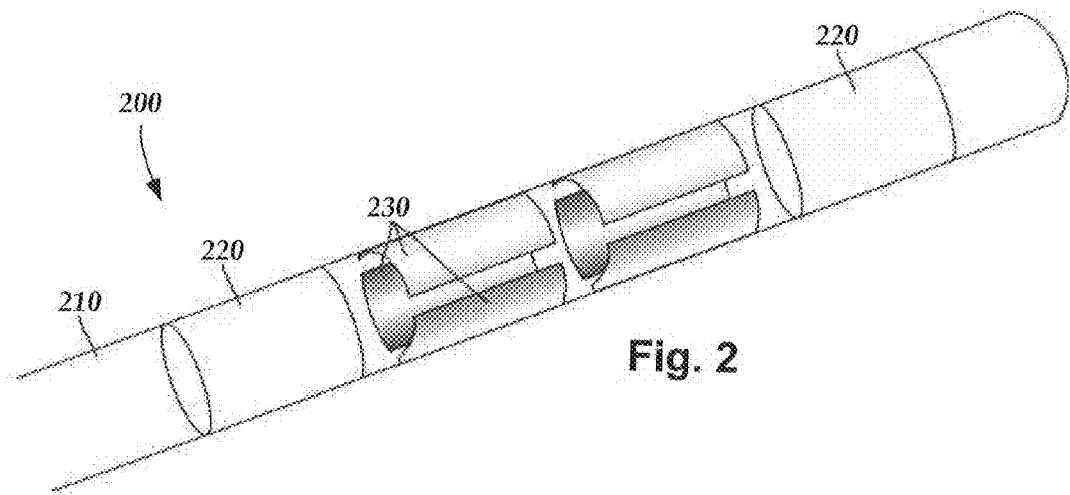
FIG. 2 is a schematic perspective view of one embodiment of a portion of a lead having a plurality of segmented electrodes, according to the invention.

FIG. 2 illustrates one embodiment of a distal portion of a lead 200 for brain stimulation. The lead 200 includes a lead body 210, one or more optional ring electrodes 220, and a plurality of sets of segmented electrodes 230. The lead body 210 can be formed of a biocompatible, non-conducting material such as, for example, a polymeric material. Suitable polymeric materials include, but are not limited to, silicone, polyurethane, polyethylene, polyurea, polyurethane-urea, or the like. Once implanted in the body, the lead 200 may be in contact with body tissue for extended periods of time. In at least some embodiments, the lead 200 has a cross-sectional diameter of no more than 1.5 mm and may be in the range of 0.5 to 1.5 mm. In at least some embodiments, the lead 200 has a length of at least 10 cm and the length of the lead 200 may be in the range of 10 to 70 cm.

The electrodes may be made using a metal, alloy, conductive oxide, or any other suitable conductive biocompatible material. Examples of suitable materials include, but, are not limited to, platinum, platinum iridium alloy, iridium, titanium, tungsten, palladium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 220 may be disposed on any part of the lead body 210, usually near a distal end of the lead 200. In FIG. 2, the lead 200 includes two ring electrodes 220. Any number of ring electrodes 220 may be disposed along the length of the lead body 210 including, for example, one, two three, four, five, six, seven, eight, nine, ten, eleven, twelve, thirteen, fourteen, fifteen, sixteen or more ring electrodes 220. It will be understood that any number of ring electrodes may be disposed along the length of the lead body 210. In some embodiments, the ring electrodes 220 are substantially cylindrical and wrap around the entire circumference of the lead body 210. In some embodiments, the outer diameters of the ring electrodes 220 are substantially equal to the outer diameter of the lead body 210. The length of the ring electrodes 220 may vary according to the desired treatment and the location of the target neurons. In some embodiments, the length of the ring electrodes 220 are less than, or equal to, the diameters of the ring electrodes 220. In other embodiments, the lengths of the ring electrodes 220 are greater than the diameters of the ring electrodes 220. In other embodiments, the lengths of the ring electrodes 220 are greater than the diameters of the ring electrodes 220. The distal-most ring electrode 220 may be a sip electrode (see e.g., tip electrode 320a of FIG. 3C) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented, electrodes include U.S. Patent Application Publication Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; and 2012/0203321, all of which are incorporated herein by reference.

In FIG. 2, the lead 200 is shown having a plurality of segmented electrodes 230. Any number of segmented electrodes 230 may be disposed on the lead body 210 including, for example, one, two three, four, five, six, seven, eight, nine, ten, eleven, twelve, thirteen, fourteen, fifteen, sixteen or more segmented electrodes 230. It will be understood that any number of segmented electrodes 230 may be disposed along the length of the lead body 210. A segmented electrode 130 typically extends only 75%, 67%, 60%, 50%, 40%, 33%, 25%, 20%, 17%, 15%, or less around the circumference of the lead.

The segmented electrodes 230 may be grouped into sets of segmented electrodes, where each set is disposed around a circumference of the lead 200 at a particular longitudinal portion of the lead 200. The lead 200 may have any number segmented electrodes 230 in a given set of segmented electrodes. The lead 200 may have one, two, three, four, five, six, seven, eight, or more segmented electrodes 230 in a given set. In at least some embodiments, each set of segmented electrodes 230 of the lead 200 contains the same number of segmented electrodes 230. The segmented electrodes 230 disposed on the lead 200 may include a different number of electrodes than at least one other set of segmented electrodes 230 disposed on the lead 200.

The segmented electrodes 230 may vary in size and shape. In some embodiments, the segmented electrodes 230 are all of the same size, shape, diameter, width or area or any combination thereof hi some embodiments, the segmented electrodes 230 of each circumferential set (or even all segmented electrodes disposed on the lead 200) may be identical in size and shape.

Each set of segmented electrodes 230 may be disposed around the circumference of the lead body 210 to form a substantially cylindrical shape around the lead body 210. The spacing between individual electrodes of a given set of the segmented electrodes may be the same, or different from, the spacing between individual electrodes of another set of segmented electrodes on the lead 200. In at least some embodiments, equal spaces, gaps, or cutouts are disposed between each segmented electrode 230 around the circumference of the lead body 210. In other embodiments, the spaces, gaps, or cutouts between the segmented electrodes 230 may differ in size or shape. In other embodiments, the spaces, gaps, or cutouts between segmented electrodes 230 may be uniform for a particular set of the segmented electrodes 230, or for all sets of the segmented electrodes 230. The sets of segmented electrodes 230 may be positioned in irregular or regular intervals along a length the lead body 210.

Conductor wires that attach to the ring electrodes 220 or segmented electrodes 230 extend along the lead body 210. These conductors may extend through the material of the lead 200 or along one or mote lumens defined by the lead 200, or both. The conductors are presented at a connector (via terminals) for coupling of the electrodes 220, 230 to a control unit (not shown).

When the lead 200 includes both ring electrodes 220 and segmented electrodes 230, the ring electrodes 220 and the segmented electrodes 230 may be arranged in any suitable configuration. For example, when the lead 200 includes two sets of ring electrodes 220 and two sets of segmented electrodes 230, the ring electrodes 220 can flank the two sets of segmented electrodes 230 (see e.g., FIG. 2).

Figure 3A:
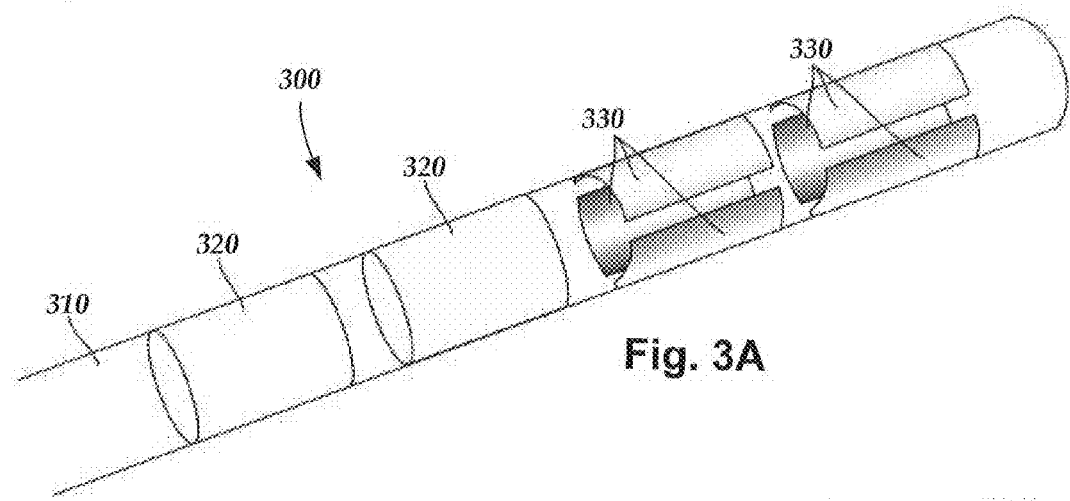
FIG. 3A is a perspective view of a second embodiment of a portion of a lead having a plurality of segmented electrodes, according to the invention.
Figure 3B:
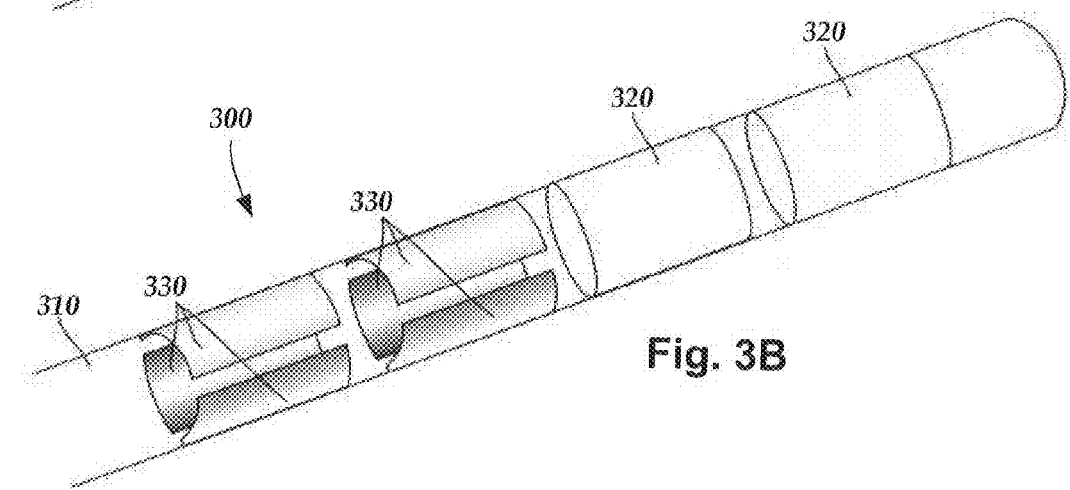
FIG. 3B is a perspective view of a third embodiment of a portion of a lead having a plurality of segmented electrodes, according to the invention.
Figure 3C:
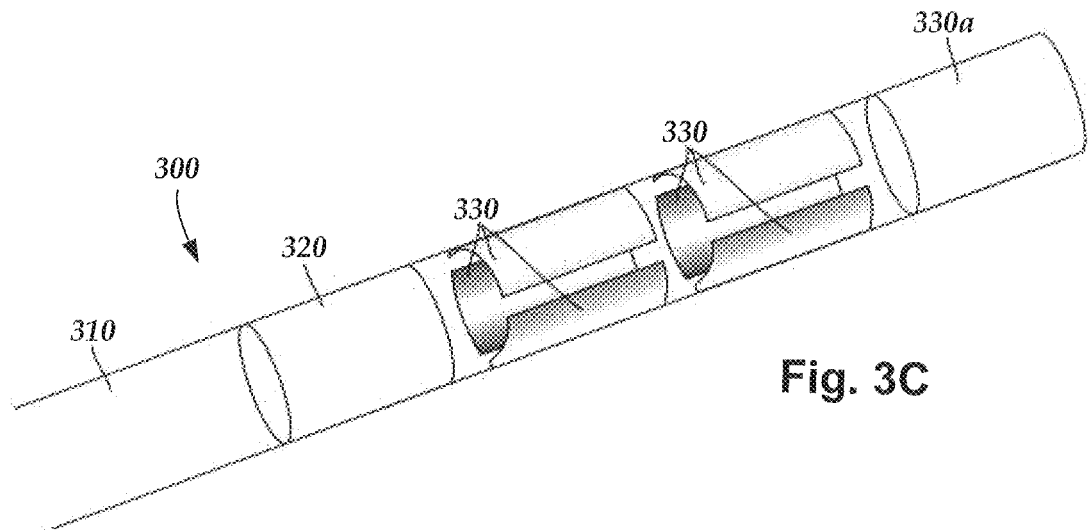
FIG. 3C is a perspective view of a fourth embodiment of a portion of a lead having a plurality of segmented electrodes, according to the invention.

Other alternate electrode configurations may be used. FIGS. 3A-3C illustrate leads 300 with segmented electrodes 330, optional ring electrodes 320 or tip electrodes 320a, and a lead body 310. The sets of segmented electrodes 330 include three segmented electrodes or any other number of segmented electrodes including, for example, two, four, five, six, or more. In each of FIGS. 3A-3C, two sets of segmented electrodes 330 and two sets of optional ring electrodes 320 are shown. Any suitable number of segmented electrodes 330, or ring electrodes 320, or both, may be used. The two sets of ring electrodes 220 can be disposed proximal to the two sets of segmented electrodes 230 (see e.g., FIG. 3A), or the two sets of ring electrodes 220 can be disposed distal to the two sets of segmented electrodes 230 (see e.g., FIG. 3B). One of the ring electrodes can be a tip electrode (see, tip electrode 320a of FIG. 3C). It will be understood that other configurations are possible as well (e.g., alternating ring and segmented electrodes, or the like). Any other suitable arrangements of segmented electrodes can be used. As an example, arrangements in which segmented electrodes are arranged helically with respect to each other. One embodiment includes a double helix.

By varying the location of the segmented electrodes 230, different coverage of the target neurons may be selected, for example, the electrode arrangement of FIG. 3A may be useful if the physician anticipates that the neural target will be closer to a distal tip of the lead body 210, while the electrode arrangement of FIG. 3B may be useful if the physician anticipates that the neural target will be closer to a proximal end of the lead body 210.

Any combination of ring electrodes 220 and segmented electrodes 230 may be disposed on the lead 200. For example, the lead may include a first ring electrode 120, two sets of segmented electrodes, where each set is formed of three segmented electrodes 230, and a final ring electrode 120 at the distal end portion (or, in the case of a tip electrode, at the distal tip of the lead). This configuration may simply be referred to as a 1-3-3-1 configuration. It may be useful to refer to the electrodes with this shorthand notation. Thus, the embodiment of FIG. 3A may be referred to as a 1-1-3-3 configuration, while the embodiment of FIG. 3B may be referred to as a 3-3-1-1 configuration. Other eight-electrode configurations include, for example, a 2-2-2-2 configuration, where four sets of segmented electrodes are disposed on the lead, and a 4-4 configuration, where two sets of segmented electrodes, each having four segmented electrodes 230 are disposed on the lead. In some embodiments, the lead, includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 4:
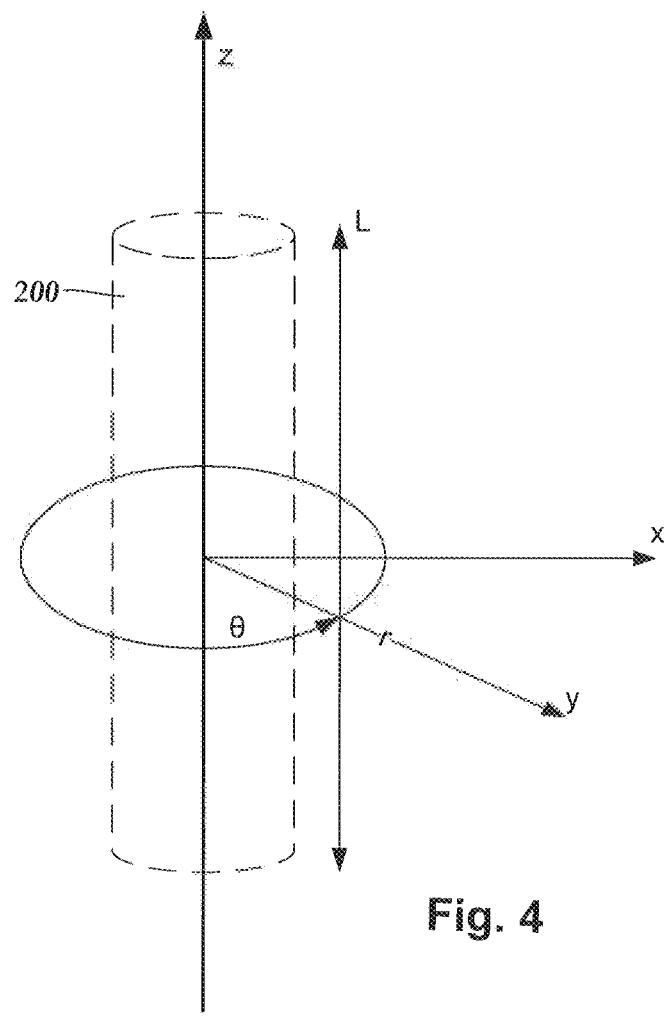
FIG. 4 is a schematic diagram of radial current steering along various electrode levels along a length of a lead, according to the invention.

FIG. 4 is a schematic diagram to illustrate radial current steering along various electrode levels along a longitudinal length of the lead 200. While conventional lead configurations with ring electrodes are only able to steer current along the longitudinal length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 4, the centroid of stimulation can be shifted at each level along the longitudinal length of the lead 200. The use of multiple sets of segmented electrodes at different levels along the longitudinal length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes, it will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

When the lead 200 includes a plurality of sets of segmented electrodes 230, it may be desirable to form the lead 200 such that corresponding electrodes of different sets of segmented electrodes 230 are radially aligned with one another along the length of the lead 200 (see e.g., the segmented electrodes 230 shown in FIG. 2). Radial alignment between corresponding electrodes of different sets of segmented electrodes 230 along the length of the lead 200 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 200 are radially aligned with one another and do not radially shift in relation to one another during manufacturing of the lead 200.

FIG. 5 is a side view of another embodiment of the lead 200 having a plurality of sets of segmented electrodes. As shown in FIG. 5, individual electrodes in the two sets of segmented electrodes 230 are staggered relative to one another along the length of the lead body 210. In some cases, the staggered positioning of corresponding electrodes of different sets of segmented electrodes along the length of the lead 200 may be designed for a specific application.

A number of issues can arise in the manufacture of leads containing segmented electrodes. For example, it may be difficult to maintain the position and spacing between segmented electrodes during or after manufacture, particularly during operations in which parts of the lead body are heated for reflow. The segmented electrodes may shift within the heated polymer, altering the spacing between segmented electrodes. Furthermore, electrode retention after manufacture may be of concern. Segmented electrodes and methods of manufacture can be designed to address these and other issues. For example, U.S. Provisional Patent Application Ser. No. 61/356,529, incorporated herein by reference, provides some examples of segmented electrodes and method of manufacture.

As herein described, the segmented electrodes can include one or more lead-retention features that facilitate retention and maintenance of the positioning and spacing of the segmented electrodes during or alter (or both during and after) manufacture. During manufacture, the lead-retention features can be at least partially filled (preferably, completely filled) with material from the lead body or other portions of the lead to facilitate maintenance of the positioning and spacing, as well as retention, of the segmented electrodes.

Sets of radially-disposed segmented electrodes can be formed from pre-electrodes. FIGS. 6A-10C illustrate embodiments of pre-electrodes and sets of segmented electrodes formed from the pre-electrodes (e.g., by grinding down the pre-electrodes to form electrically isolated segmented electrodes). The pre-electrodes, and segmented electrodes formed therefrom, may be formed of an electrical conductor such as a metal, alloy, conductive oxide, or any other suitable conductive material. In some embodiments, the pre-electrodes are formed of platinum, platinum-iridium, iridium, 616L stainless steel (or any other suitable stainless steel), tantalum, Nitinol, iridium rhodium, or a conductive polymer.

In some embodiments, the pre-electrodes are substantially-cylindrical and have a diameter larger than the desired final diameter of a lead. A lead with a cylindrical cross-sectional profile may be obtained by grinding (e.g., center-less grinding), machining, etching, or ablating outer surfaces of the pre-electrodes. The grinding can also release the individual segmented electrodes. In FIGS. 6A-10C three segmented electrodes are shown formed from each pre-electrode. It will be recognized that other embodiments of pre-electrodes can have two, four, five, six, seven, eight, or more segmented electrodes.

FIGS. 6A-6C illustrate embodiments of a pre-electrode 600. FIGS. 6A and 6C show transverse cross-sectional views of the pre-electrode, and FIG. 6B shows a perspective view of the pre-electrode. The pre-electrode 600 includes a body 602 having an interior surface 604 and an outer surface (i.e., a transverse circumference) 606. As shown in FIG. 6B, the pre-electrode 600 also includes a proximal end 608 and a distal end 610. In some embodiments, the body 604 of the pre-electrode 600 is substantially-cylindrical and has a diameter larger than the desired final diameter of a lead upon, which the pre-electrode 600 is disposed.

The proximal and distal ends of the pre-electrodes correspond to the orientation of the pre-electrode when disposed on a lead. For example, when the pre-electrode is disposed on a lead, the proximal end of the pre-electrode is closest to the proximal end portion of the lead. In which case, when the pre-electrode is disposed on a lead, the transverse cross-sectional view of the pre-electrode would also be transverse to a longitudinal length of the lead. It will be understood that this orientation of the pre-electrodes, as well as the orientation of the pre-electrodes when disposed on leads, applies to each of the pre-electrodes discussed herein.

The pre-electrode 600 includes individual segmented, electrodes 612 joined by connecting material 614. The connecting material 614 can be removed (for example, by grinding, machining, etching, ablating, or otherwise removing the connecting material 614) to leave the separated segmented electrodes 612 when the pre-electrode is in place on the lead.

The pre-electrode 600 defines cutouts 616 between the individual segmented electrodes, which typically define the spacing between the segmented electrodes of a particular set of segmented electrodes. The connecting material 614 may correspond only to the material between the segmented electrodes 612 or may include other portions of the pre-electrode 600 (e.g., an outer ring, or rim, of material that can be ground away to release the underlying segmented electrodes).

The cutouts can function as lead-retention features by allowing material, such as material from the lead body (including spacers positioned, for example, between sets of segmented electrodes or between a set of segmented electrodes and a ring electrode) or other material, to be placed, or flowed, into the cutouts. The material within the cutouts can also facilitate maintenance of the positioning and spacing of the segmented electrode.

The cutouts 616 have perimeters 617 extending between adjacent portions of the interior surface 604 of the pre-electrode 600. The perimeter 617 can be continuous or discontinuous. In some embodiments, the perimeter 617 of at least one of the cutouts forms a continuous surface extending between two portions of the interior surface 604 of the pre-electrode (see e.g., FIG. 6A). In other embodiments, the perimeter 617 of at least one of the cutouts forms a discontinuous surface, where the perimeter is discontinuous due to an alignment slit 640 (see e.g., FIG. 6C) along a lateral (e.g., toward the outer edge) portion of the cutout. Similarly, the pre-electrodes 700, 800, 900, and 1000 are each shown and described as having perimeters that can be either continuous or discontinuous.

Each cutout abuts two segmented electrodes with portions of the perimeter 617 forming side-walls of those segmented electrodes. In at least some embodiments, the perimeter of at least one of the cutouts is shaped such that one or more open cavities (e.g., nooks, notches, voids, indentations, open spaces, or the like or combinations thereof) are formed along at least a portion of the side-wall of at least one of the segmented electrodes abutting that cutout.

The one or more open cavities may enhance lead retention by facilitating adhesion of the material of the lead body to the pre-electrode (prior to removal of the connecting material), and to the segmented electrodes (after removal of the connecting material). In at least some embodiments, the open cavities are configured to receive and partially retain a portion of one or more conductors (see e.g., FIGS. 7A-7C). In at least some embodiments, the one or more of the open cavities provide one or more electrical coupling interfaces for coupling one or more portions of one or more conductors to a particular segmented electrode (see e.g., FIG. 7C).

FIGS. 6A-6C illustrate cutouts mat are clover-shaped in transverse cross-section with multi-lobed perimeters 617 that define a lateral lobe 618 and one or more side lubes 620. The side lobes 620 are configured to form opposing cavities (620 in FIGS. 6D-6E) defined along side-walls (622a and 622b in FIGS. 6D-6E) of abutting segmented electrodes 612. The lateral lobe 618 is positioned along a lateral periphery of the cutout 616 such that, when the connecting material 614 is removed, the lateral lobe 618 opens to the outer surface 606 of the pre-electrode. In at least some embodiments, the lateral lobe 618 extends at least partially into the connecting material 614 such that, when the connecting material 614 is removed the lateral lobe 618 is at least partially removed along with the connecting material 614. In at least some embodiments, when the connecting material 614 is removed the one or more side lobes 620 remain intact.

The pre-electrode 600 further includes one or more channels 628 formed in the segmented electrodes 612. There may be one, two, three, four, or more channels formed in each of the segmented electrodes. The number of channels in each segmented electrode may be the same or different from the number of channels in other segmented electrodes.

The one or more channels can function as lead-retention features by allowing material, such as material from the lead body (including spacers positioned, for example, between sets of segmented electrodes or between a set of segmented electrodes and a ring electrode) or other material, to be placed, or flowed, into the channels. The material within the channels can also facilitate maintenance of the positioning and spacing of the segmented electrode.

In at least some embodiments, the one or more channels are defined along the interior surface 604 of the body 602. In FIG. 6A, the one or more channels 628 have arcuate transverse cross-sectional shapes that open to the interior surface 604 of the body 602 with a portion of a perimeter of the channel surrounded by the segmented electrode. In at least some embodiments, the one or more channels 628 have a cross-sectional shape that is open to the interior surface 604 of the body 602 with at least half of the perimeter of the channel surrounded by the segmented electrode.

It will be recognized that other embodiments, similar to those illustrated in FIGS. 6A-10C, could include channels with other regular or irregular cross-sectional shapes including, but not limited to, oval, triangular, square, rectangular, pentagonal, hexagonal, octagonal, "T"-shaped, "L"-shaped, and other cross-sectional shapes. It will be recognized that the transverse cross-sectional shape of the channel need not be uniform along the length of the channel. It will be further recognized that the channels need not be identical and that different segmented electrodes may have differently shaped, channels or that channels in a particular segmented electrode may be differently shaped. In some embodiments, the channels do not extend fully through the segmented electrode along a radial direction, but only extend partially (e.g., one half or one third of the radial distance) through the segmented electrode.

In some instances, the outer surface of the pre-electrode may be uniform. In which case, the positioning of the segmented, electrodes beneath may not be apparent when viewing the pre-electrode from the side (i.e., through the outer surface from a position exterior to the pre-electrode). It may be advantageous to be able to determine the alignment of the segmented electrodes along the pre-electrode in order to position the segmented electrodes along the lead in a desired configuration.

Alignment of the segmented electrodes may be particularly relevant when aligning multiple pre-electrodes with one another along a longitudinal length of the lead. In which case, it may be desirable to form the lead such that corresponding electrodes of different sets of segmented electrodes axe rotationally aligned (see e.g., the segmented electrodes 230 shown in FIG. 2), or rotationally staggered (see e.g., the segmented electrodes 230 shown in FIGS. 3A-3B) with respect to one another along the longitudinal length of the lead. Rotational alignment (or rotational staggering) between corresponding electrodes of different sets of segmented electrodes along the longitudinal length of the lead may reduce uncertainty as to the location or orientation between corresponding segmented electrodes of different sets of segmented electrodes. Accordingly, it may be beneficial to form electrode arrays such that corresponding electrodes of different sets of segmented electrodes along the longitudinal length of the lead are rotationally aligned (or rotationally staggered) with one another during manufacturing of the lead.

In at least some embodiments, the pre-electrode includes one or more alignment features for enabling the rotational positioning of the segmented electrodes of the pre-electrode to be apparent when viewing the pre-electrode from the side. In at least some embodiments, the alignment feature forms an opening extending between the outer surface of the pre-electrode and one of the cutouts.

In at least some embodiments, the alignment feature includes one or more alignment apertures. In FIG. 6B, the pre-electrode 600 is shown defining one or more alignment apertures 630 extending between the outer surface 606 of the body 603 and one of the cutouts 616. The one or more alignment apertures do not extend an entire distance between the proximal end and the distal end of the pre-electrode. In FIG. 6B, the alignment aperture 630 is shown extending into the main lobe 618 of the cutout 616. In at least some embodiments, the one or more alignment apertures are positioned such that removal of the connecting material causes a corresponding removal of the one or more alignment apertures without affecting the shape of any of the formed segmented electrodes.

In at least some embodiments, the alignment feature includes one or more alignment slits. FIG. 6C shows one embodiment of the pre-electrode 600 defining an alignment slit 640. The alignment slit 640 is disposed along one of the cutouts 616 and extends along the entire length of the cutout 616 between the proximal end 608 and the distal end 610 of the body 602, effectively making the body 602 of the pre-electrode 600 open-loop, or C-shaped (i.e., the transverse cross-sectional circumference, or outer surface 606, of the pre-electrode is discontinuous).

In at least some embodiments, the alignment slit 640 is entirely disposed along one of the cutouts 616. In which case, when the connecting material 614 of the pre-electrode 600 is removed the alignment slit 640 is entirely disposed within the spacing between two segmented electrodes of the set of segmented electrodes formed along the pre-electrode 600. Additionally, when the alignment slit 640 is entirely disposed along one of the cutouts 616 removal of the connecting material 614 causes a corresponding removal of the alignment slit 640 without affecting the shape of any of the Firmed segmented electrodes.

As mentioned above, conductors typically extend along a longitudinal length of the lead upon which the pre-electrode is disposed. The conductors electrically couple electrodes (e.g., segmented electrodes, ring electrodes, tip electrodes, and the like) disposed along a distal end portion of the lead to terminals disposed along a proximal end portion of the lead. Depending on the relative positioning of a given pre-electrode along the lead, one or more conductors may extend through the pre-electrode and couple to other electrodes (e.g., electrodes of other pre-electrodes, ring electrodes, tip electrodes, or the like or combinations thereof). In which case, it may be advantageous to form the pre-electrode with an alignment slit so that, during manufacturing, one or more of the conductors can be passed through the alignment slit without needing to string the ends of the one or more conductors through the pre-electrode to reach other electrodes.

FIG. 6D illustrates, in transverse cross section, the set of segmented electrodes 612 formed after removal of the connecting material 614 of the pre-electrode 600. The segmented electrodes 612 include the interior surface 604, an opposing exterior surface 656, and opposing side-walls 622a and 622b each extending radially between the interior surface 604 and the exterior surface 656. It will be understood that, although not shown in FIG. 6D, the segmented electrodes 612 also include a proximal end and an opposing distal end. These proximal and distal ends are typically the same as the proximal and distal ends of the pre-electrode. For example, in at least some embodiments the proximal and distal ends of the segmented electrodes 612 are the same as the proximal and distal ends of the pre-electrode 600 shown in FIG. 6B. In at least some embodiments, each of the interior surface 604, the exterior surface 656, and the side-walls 622a and 622b extend from the proximal end to the distal end of the pre-electrode.

The interior surfaces 604 of the segmented electrodes 612 are typically defined by the interior surface 604 of the pre-electrode 600. The opposing side-walls 622a and 622b are typically defined by portions of the perimeters 617 of the cutouts 616. In at least some embodiments, when removing the connecting material 614, portions of the perimeter 617 of the cutouts 616 (particularly the lateral-most portions of the perimeter 617) may be removed along with the connecting material 614. The exterior surfaces 656 of the segmented electrodes 612 are formed from inner portions of the body 602 of the pre-electrode 600 that previously abutted the connecting material 614 prior to removal of the connecting material 614.

At least one open cavity is defined along at least one of the side-walls of at least one of the segmented electrodes. In at least some embodiments, two, three, four, or more open cavities are defined along at least one of the side-walls of at least one of the segmented electrodes. In FIG. 6D, open cavities are defined by the side lobes 620 of the multi-lobed cutouts. In FIG. 6D, these open cavities are defined along both side-walls 622a and 622b of each of the segmented electrodes 612.

In at least some embodiments, open cavities extend along the entire dimension of the segmented electrode from the proximal end to the distal end. Open cavities do not extend an entire circumferential length of a segmented electrode between opposing side-walls. Additionally, when open cavities extend circumferentially inwardly along opposing side-walls, the open cavities of the opposing side-walls do not open to one another. It will be understood that the above description of open cavities applies to all of the open cavities described herein.

It may be advantageous for the open cavities to not extend an entire circumferential length of a segmented electrode between opposing side-walls. Extending the open cavities an entire circumferential length of a segmented electrode between opposing side-walls may reduce the integrity of the segmented electrodes to a potentially unsafe level. Additionally, in embodiments where the open cavities extend along the entire dimension of the segmented electrode from the proximal end to the distal end, were the open cavities to also extend the entire circumferential length of a segmented electrode between opposing side-walls then the segmented electrodes would be undesirably split into two discrete pieces. Moreover, extending the open cavities an entire circumferential length of a segmented electrode between opposing side-walls may make it difficult to remove air pockets when flowing or molding lead material or spaces around the segmented electrodes.

FIG. 6E illustrates, in transverse cross section, the set of segmented electrodes 612, as shown in FIG. 6D, disposed along a lead body 672. In FIG. 6E, the lead body 672 includes a longitudinal surface 676. Optionally, the lead body 672 defines one or more lumens 680 extending along a longitudinal length of the lead body 672 and configured to receive a stylet (see e.g., 140 in FIG. 1). In at least some embodiments, the segmented electrodes 612 are equally spaced-apart from one another around a transverse circumference of the lead body 672. The exterior surfaces 656 of one or more of the segmented electrodes 612 can be inset from, or extended outwardly from, the longitudinal surface 676 of the lead body 672. In FIG. 6E, the exterior surfaces 656 of each of the segmented electrodes 612 are shown flush with the longitudinal surface 676 of the lead body 672. It may be advantageous for the exterior surfaces 656 of each of the segmented electrodes 612 to be flush with the longitudinal surface 676 of the lead body 672 in order to maintain an isodiametric profile along a distal end portion of the lead body, thereby reducing the risk of patient tissue getting caught along the lead body daring lead insertion.

Figure 7A:
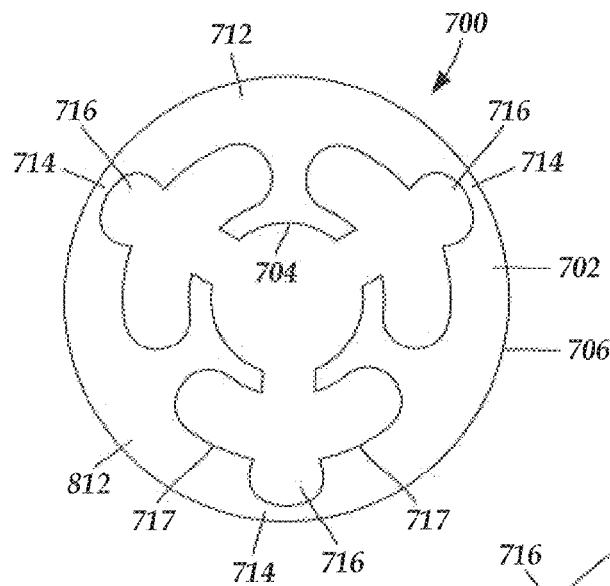
FIG. 7A is a schematic transverse cross-sectional view of a second embodiment of a pre-electrode having a cutout with side open cavities configured and arranged to receive one or more conductors, according to the invention.
Figure 7B:
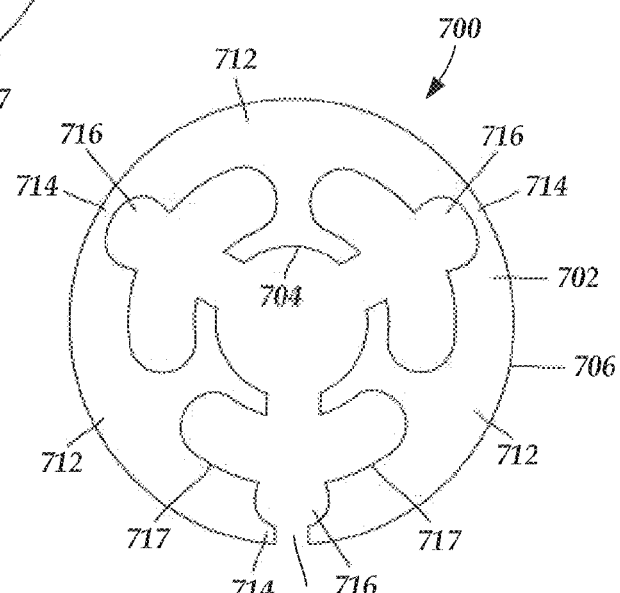
FIG. 7B is a schematic transverse cross-sectional view of one embodiment of the pre-electrode of FIG. 7A with an alignment slit defined along a cutout of the pre-electrode, according to the invention.
Figure 7C:
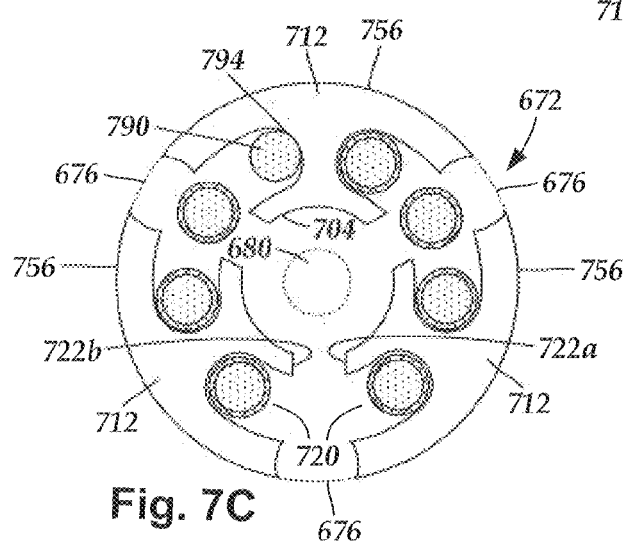
FIG. 7C is a schematic transverse cross-sectional view of one embodiment of a set of segmented electrodes formed by removing connecting material of the pre-electrode of FIG. 7A or FIG. 7B, the set of segmented electrodes disposed along a lead body, according to the invention.

Turning to FIGS. 7A-7C, in at least some embodiments the open cavities of the segmented electrodes are configured to receive and partially retain at least a portion of one or mote conductors extending along the lead (e.g., conductors electrically coupling the electrodes to the terminals). In at least some embodiments, the open cavities also provide electrical coupling interfaces for electrically coupling one or more conductors to the segmented electrodes.

FIGS. 7A-7B illustrate schematic transverse cross-sectional views of alternate embodiments of a pre-electrode 700. The pre-electrode 700 includes a body 702 that has an interior surface 704, an outer surface 706, and that defines cutouts 716. The pre-electrode 700 includes individual segmented electrodes 712 joined by connecting material 714 that can be removed (for example, by grinding, machining, etching, ablating, laser cutting, or otherwise removing the connecting material 714) to leave the separated segmented electrodes 712 when the pre-electrode is in place on the lead.

In FIG. 7A, the body 702 of the pre-electrode 700 has a closed-loop transverse circumference. In FIG. 7B, the body 702 defines an alignment slit 740. The alignment slit 740 is disposed along one of the cutouts 716 and extends along the entire length of the cutout 716 between a proximal end and a distal end of the body 702, effectively making the body 702 of the pre-electrode 700 open-loop, or C-shaped (i.e., the cross-sectional circumference, or outer surface 706, of the pre-electrode is discontinuous).

In at least some embodiments, the alignment slit 740 is entirely disposed along one of the cutouts 716. In which case, when the connecting material 714 of the pre-electrode 700 is removed the alignment slit 740 may be at least partially disposed within the spacing between two segmented electrodes of the set of segmented electrodes formed along the pre-electrode 700. In at least some embodiments, when the connecting material 714 of the pre-electrode 700 is removed the alignment slit 740 is entirely disposed within the spacing between two segmented electrodes of the set of segmented electrodes formed along the pre-electrode 700. In at least some embodiments, the alignment slit 740 is positioned such that removal of the connecting material 714 causes a corresponding removal of the alignment slit 740 without affecting the shape of any of the formed segmented electrodes.

The cutouts 716 have perimeters 717 extending between adjacent portions of the interior surface 704 of the pre-electrode 700. Each cutout abuts two segmented electrodes with portions of the perimeter 717 forming side-walls of those segmented electrodes. The perimeter 717 of at least one of the cutouts is shaped such that one or more open cavities are formed along at least a portion of the side-wall of at least one of the segmented electrodes abutting that cutout.

FIGS. 7A-7C illustrate cutouts that are clover-shaped in transverse cross-section with multi-lobed perimeters 717 that define a lateral lobe and one or more side lobes. The side lobes are configured to form opposing cavities (720 in FIG. 7C) defined along side-walls (722a and 722b in FIG. 7C) of abutting segmented electrodes 712.

FIG. 7C illustrates, in transverse cross-section, the set of segmented electrodes 712 formed after removal of the connecting material 914 of the pre-electrode 900. The set of segmented electrodes 712 are disposed along the lead body 672. The segmented electrodes 712 include the interior surface 704, an exterior surface 756, and opposing side-walls 722a and 722b, extending radially between the interior surface 704 and the exterior surface 756. It will be understood that, although not shown in FIG. 7C, the segmented electrodes 712 also include a proximal end and an opposing distal end. These proximal and distal ends are typically the same proximal and distal ends as that of the pre-electrode along which the segmented are disposed (see e.g., FIG. 6B).

The interior surfaces 704 of the segmented electrodes 712 are typically defined by the interior surface 704 of the pre-electrode 700. The opposing side-walls 722a and 722b are typically defined by portions of the perimeters 717 of the cutouts 716. In at least some embodiments, when removing the connecting material 714, portions of the perimeter 717 of the cutouts 716 (particularly the lateral-most portions of the perimeter 717) may be removed along with the connecting material 714. The exterior surfaces 756 of the segmented electrodes 712 are formed from inner portions of the body 702 of the pre-electrode 700 that previously abutted the connecting material 714 prior to removal of the connecting material 714.

In FIG. 7C, the lead body 672 includes the longitudinal surface 676. Optionally, the lead body 672 defines one or more lumens 680 extending along a longitudinal length of the lead body 672 and configured to receive a stylet (see e.g., 140 in FIG. 1). In at least some embodiments, the segmented electrodes 712 are equally spaced-apart from one another around a transverse circumference of the lead body 672. The exterior surfaces 756 of one or more of the segmented electrodes 612 can be inset from, or extended outwardly from, the longitudinal surface 676 of the lead body 672. In FIG. 7C, the exterior surfaces 756 of each of the segmented electrodes 712 are shown flush with the longitudinal surface 676 of the lead body 672. It may be advantageous for the exterior surfaces 756 of each of the segmented electrodes 712 to be flush with the longitudinal surface 776 of the lead body 772 in order to maintain an isodiametric profile along a distal end portion of the lead body, thereby reducing the risk of patient tissue getting caught along the lead body during lead insertion.

At least one open cavity 720 is defined along at least one of the side-walls 722a or 722b of at least one of the segmented electrodes 712. In FIG. 7C, open cavities are defined by the side lobes of the multi-lobed cutouts. In FIG. 7C, these open cavities are defined along both side-walls 722a and 722b of each of the segmented electrodes 712. The open cavities 720 extend along the entire dimension of the segmented electrode from the proximal end to the distal end. The open cavities do not extend an entire circumferential length of a segmented electrode between opposing side-walls. Additionally, when the open cavities extend circumferentially inwardly along opposing side-walls, the open cavities of the opposing side-walls do not open to one another.

In at least some embodiments, at least one of the open cavities is configured to receive, and at least partially retain, at least one conductor (e.g., a conductor extending between one or more of the electrodes and one or more of the terminals disposed along opposing end portions of the lead). In at least some embodiments, each of the open cavities 720 are configured to receive, and at least partially retain, at least one conductor. In at least some embodiments, at least one of the open cavities 720 is configured to receive, and at least partially retain, at least two, three, four, or more conductors.

In FIG. 7C, conductors, such as conductor 790, are shown extending along the lead body 672 and received, and at least partially retained, by at least one of the open cavities 720. In FIG. 7C, each open cavity 720 is shown receiving a different conductor 790. Additionally, FIG. 7C shows some conductors disposed in a center portion of the cutout 716 between open cavities 720 of two different segmented electrodes 712. Typically, the conductors 790 are coated with an electrically insulative material. In at least some embodiments, at least one of the conductors 790 is electrically coupled to at least one of the segmented electrodes, via an electrical coupling interface 794 disposed along the side-wall 722a and 722b within, or in immediate proximity to, the open cavity 720.

Figure 8A:
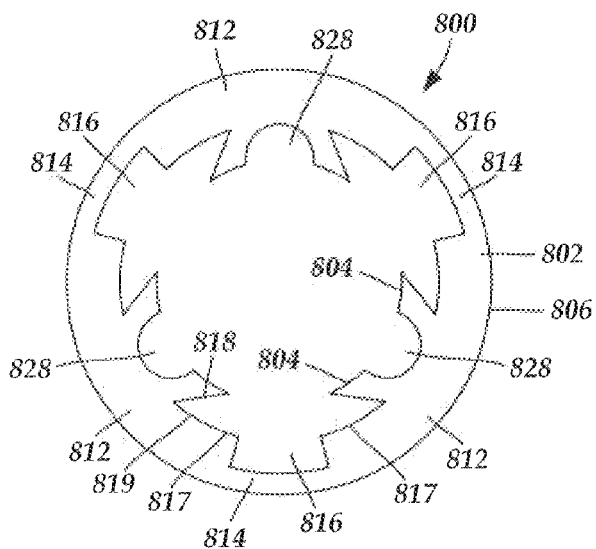
FIG. 8A is a schematic transverse cross-sectional view of a third embodiment of a pre-electrode having cutouts with pointed side open cavities, according to the invention.
Figure 8B:
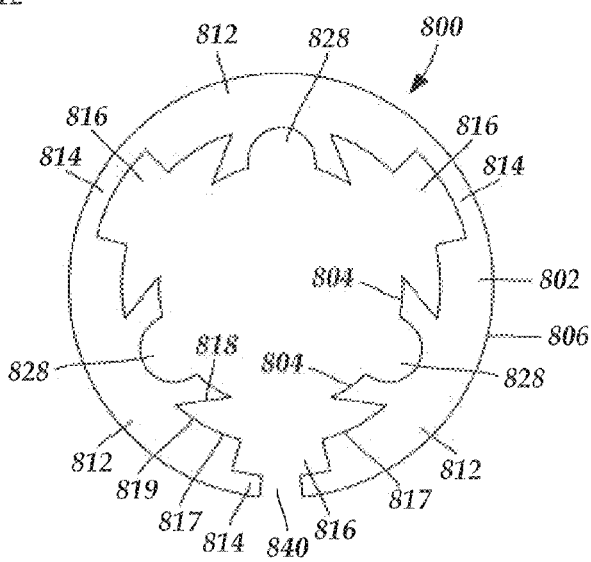
FIG. 8B is a schematic transverse cross-sectional view of one embodiment of the pre-electrode of FIG. 8A with an alignment slit defined along a cutout of the pre-electrode, according to the invention.
Figure 8C:
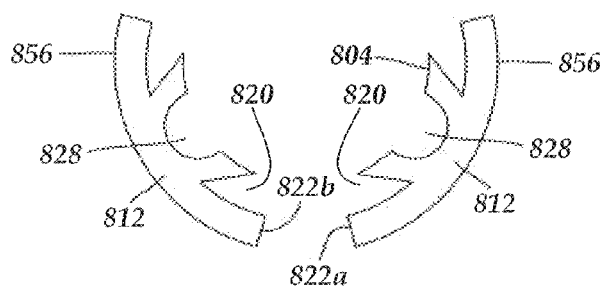
FIG. 8C is a schematic transverse cross-sectional view of one embodiment of a set of segmented electrodes formed by removing connecting material of the pre-electrode of FIG. 8A or FIG. 8B, according to the invention.

Turning to FIGS. 8A-8C, in at least some embodiments the segmented electrodes formed from the pre-electrode define open cavities with transverse cross-sectional profiles that are pointed. Forming open cavities with one or more points may improve adhesion between the segmented electrodes and the lead body. FIGS. 8A-8B illustrate schematic transverse cross-sectional views of embodiments of a pre-electrode 800. The pre-electrode 800 includes a body 802 that has an interior surface 804, an outer surface 806, and that defines cutouts 816. The pre-electrode 800 includes individual segmented electrodes 812 joined by connecting material 814 that can be removed (for example, by grinding, machining, etching, ablating, laser cutting, or otherwise removing the connecting material 814) to leave the separated segmented electrodes 812 when the pre-electrode is in place on the lead. The pre-electrode 800 further includes one or more channels 828 formed along the interior surfaces 804 of the segmented electrodes 812 and extending from a proximal end of the pre-electrode to a distal end of the pre-electrode. In FIGS. 8A-8C, the channels 828 are shown having a "U"-shaped transverse cross-sectional profile.

In FIG. 8A, the body 802 of the pre-electrode 800 has a closed-loop transverse circumference. In FIG. 8B, the body 802 defines an alignment slit 840. The alignment slit 840 is disposed along one of the cutouts 816 and extends along the entire length of the cutout 816 between a proximal end and a distal end of the body 802, effectively making the body 802 of the pre-electrode 800 open-loop, or C-shaped (i.e., the cross-sectional circumference, or outer surface 806, of the pre-electrode is discontinuous).

In at least some embodiments, the alignment slit 840 is entirely disposed along one of the cutouts 816. In which case, when the connecting material 814 of the pre-electrode 800 is removed the alignment slit 840 may be at least partially disposed within the spacing between two segmented electrodes of the set of segmented electrodes formed along the pre-electrode 800. In at least some embodiments, when the connecting material 814 of the pre-electrode 800 is removed the alignment slit 840 is entirely disposed within the spacing between two segmented electrodes of the set of segmented electrodes formed along the pre-electrode 800. In at least some embodiments, the alignment slit 840 is positioned such that removal of the connecting material 814 causes a corresponding removal of the alignment slit 840 without affecting the shape of any of the formed segmented electrodes.

The cutouts 816 have perimeters 817 extending between adjacent portions of the interior surface 804 of the pre-electrode 800. Each cutout abuts two segmented electrodes with portions of the perimeter 817 forming side-walls of those segmented electrodes. The perimeter 817 of at least one of the cutouts is shaped such that one or more open cavities are formed along at least a portion of the side-wall of at least one of the segmented electrodes abutting that cutout.

FIGS. 8A-8C illustrate cutouts with perimeters 817 that include medial portions 818 (that are continuous with the interior surface 804 of the pre-electrode) and lateral portions 819 (that are partially removed along with the connecting material 814 and) that intersect along at least one of the open cavities 820 to form an internal ridge extending between the proximal and distal ends of the pre-electrode. Note that the internal ridge forms a "point" when shown in transverse cross-section. It may be an advantage to form the open cavities 820 with internal ridges (or points in cross-section) to improve adhesion of the lead body to the segmented electrodes of the pre-electrode.

FIG. 8C illustrates, in transverse cross section, the set of segmented electrodes 812 formed after removal of the connecting material 814 of the pre-electrode 800. The segmented electrodes 812 include the interior surface 804, an exterior surface 856, and opposing side-walls 822a and 822b extending radially between the interior surface 804 and the exterior surface 856. It will be understood that, although not shown in FIG. 8C, the segmented electrodes 812 also include a proximal end and an opposing distal end. These proximal and distal ends are typically the same proximal and distal ends as that of the pre-electrode along which the segmented are disposed (see e.g., FIG. 6B).

The interior surfaces 804 of the segmented electrodes 812 are typically the same surfaces as the interior surface 804 of the pre-electrode 800. The opposing side-walls 822a and 822b are typically defined by portions of the perimeters 817 of the cutouts 816. In at least some embodiments, when removing the connecting material 814, portions of the perimeter 817 of the cutouts 816 (particularly the lateral-most portions of the perimeter 817) may be removed along with the connecting material 814. The exterior surfaces 856 of the segmented electrodes 812 are formed from inner portions of the body 802 of the pre-electrode 800 that previously abutted the connecting material 814 prior to removal of the connecting material 814.

At least one open cavity 820 is defined along at least one of the side-walls 822a or 822b of at least one of the segmented electrodes 812. In FIG. 8C, open cavities are defined along both side-walls 822a and 822b of each of the segmented electrodes 812. The open cavities 820 extend along die entire dimension of the segmented electrode from the proximal end to the distal end. The open cavities do not extend an entire circumferential length of a segmented electrode between opposing side-walls. Additionally, when the open cavities extend circumferentially inwardly along opposing side-walls, the open cavities of the opposing side-walls do not open to one another.

Turning to FIGS. 9A-9D, in at least some embodiments the one or more channels extend along a substantial portion of a circumferential distance between adjacent cutouts. In at least some embodiments, the segmented electrodes formed from the pre-electrode have angles formed between the side-walls and the exterior surface that facilitate adhesion between the segmented electrodes and the material of the lead body. In at least some embodiments the pre-electrode includes an alignment feature formed as at least one alignment tab.

Figure 9A:
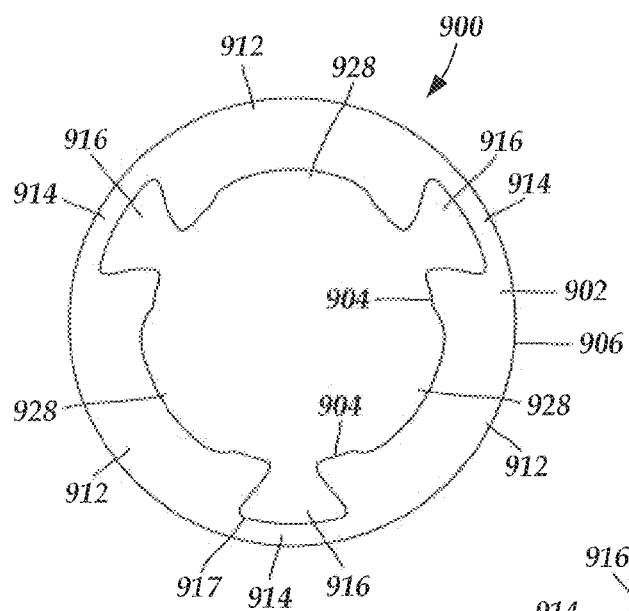
FIG. 9A is a schematic transverse cross-sectional view of a fourth embodiment of a pre-electrode having a wide channel extending between adjacent cutouts, according to the invention.
Figure 9B:
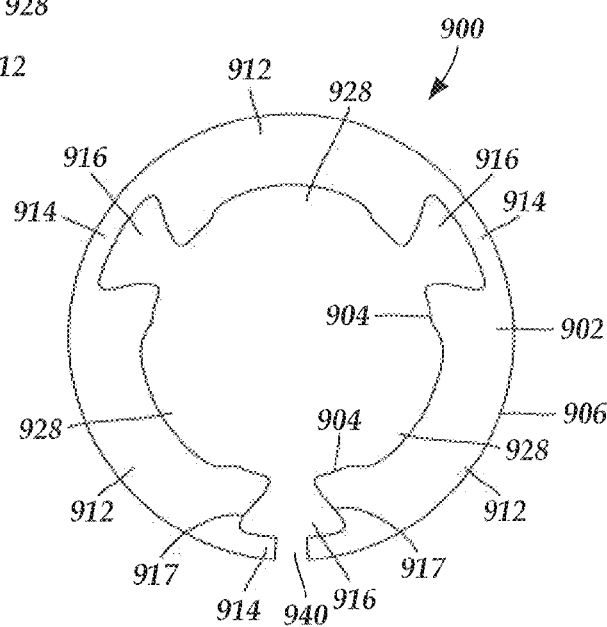
FIG. 9B is a schematic transverse cross-sectional view of one embodiment of the pre-electrode of FIG. 9A with an alignment slit defined along a cutout of the pre-electrode, according to the invention.

FIGS. 9A-9B illustrate schematic transverse cross-sectional views of embodiments of a pre-electrode 900. The pre-electrode 900 includes a body 902 that has an interior surface 904, an outer surface 906, and that defines cutouts 916. The pre-electrode 900 includes individual segmented, electrodes 912 joined by connecting material 914 that can be removed (for example, by grinding, machining, etching, ablating, or otherwise removing the connecting material 914) to leave the separated segmented electrodes 912 when the pre-electrode is in place on the lead. The cutouts 916 have perimeters 917 extending between different portions of the interior surface 904 of the pre-electrode 900. Each cutout abuts two segmented electrodes with portions of the perimeter 917 forming side-walls of those segmented electrodes.

In FIG. 9A, the body 902 of the pre-electrode 900 has a closed-loop transverse circumference. In FIG. 9B, the body 902 defines an alignment slit 940. The alignment slit 940 is disposed along one of the cutouts 916 and extends along the entire length of the cutout 916 between a proximal end and a distal end of the body 902, effectively making the body 902 of the pre-electrode 900 open-loop, or C-shaped (i.e., the cross-sectional circumference, or outer surface 906, of the pre-electrode is discontinuous).

In at least some embodiments, the alignment slit 940 is entirely disposed along one of the cutouts 916. In which case, when the connecting material 914 of the pre-electrode 900 is removed the alignment slit 940 may be at least partially disposed within the spacing between two segmented electrodes of the set of segmented electrodes formed along the pre-electrode 900. In at least some embodiments, when the connecting material 914 of the pre-electrode 900 is removed the alignment slit 940 is entirely disposed within the spacing between two segmented electrodes of the set of segmented electrodes formed along the pre-electrode 900. In at least some embodiments, the alignment slit 940 is positioned such that removal of the connecting material 914 causes a corresponding removal of the alignment slit 940 without affecting the shape of any of the formed segmented electrodes.

Figure 9C:
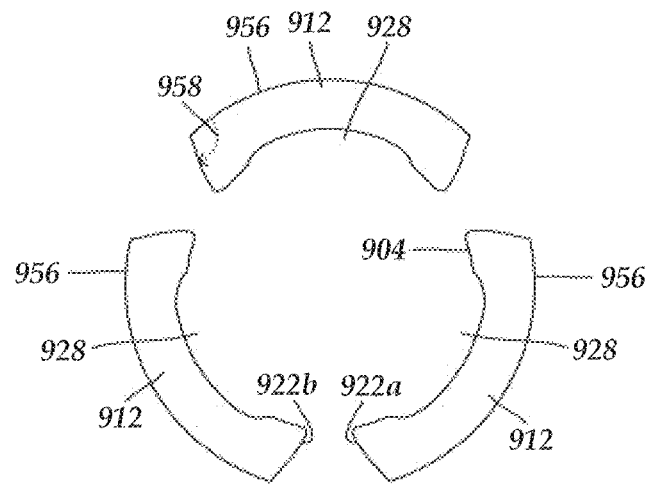
FIG. 9C is a schematic transverse cross-sectional view of one embodiment of a set of segmented electrodes formed by removing connecting material of the pre-electrode of FIG. 9A or FIG. 9B, according to the invention.

The pre-electrode 900 further includes one or more channels 928 formed in the segmented electrodes 912. In FIGS. 9A-9C, the channels 928 extend along the interior surface 904 of the pre-electrode 900 between flanking cutouts 916 such that the channels 928 extend along at least 30%, 40%, 50%, 60%, 70%, 80%, 90%, or more of a circumferential distance between flanking cutouts 916.

FIG. 9C illustrates, in transverse cross section, the set of segmented electrodes 912 formed after removal of the connecting material 914 of the pre-electrode 900. The segmented electrodes 912 include the interior surface 904, an exterior surface 956, and opposing side-walls 922a and 922b extending radially between the interior surface 904 and the exterior surface 956. It will be understood that, although not shown in FIG. 9C, the segmented electrodes 912 also include a proximal end and an opposing distal end. These proximal and distal ends are typically the same proximal and distal ends as that of the pre-electrode along which the segmented are disposed (see e.g., FIG. 6B).

The interior surfaces 904 of the segmented electrodes 912 are typically the same surfaces as the inferior surface 904 of the pre-electrode 900. When the segmented electrodes are separated from one another, the channels 928 extend along the interior surface 904 of at least one of the segmented electrodes 912 such that the channels 928 extend along at least 30%, 40%, 50%, 60%, 70%, 80%, 90%, or more of a circumferential length of the inferior surface 904 of the segmented electrode.

The opposing side-walls 922a and 922b are typically defined by portions of the perimeters 917 of the cutouts 916. In at least some embodiment, when removing the connecting material 914, portions of the perimeter 917 of the cutouts 916 (particularly the lateral-most portions of the perimeter 917) may be removed along with the connecting material 914. The exterior surfaces 956 of the segmented electrodes 912 are formed from inner portions of the body 902 of the pre-electrode 900 that previously abutted the connecting material 914 prior to removal of the connecting material 914.

In at least some embodiments, the side-walls of the segmented electrodes are angled such that, when the connecting material 914 is removed, the angling of the side-walls facilitates adhesion between the segmented electrodes and the material of the lead body. In at least some embodiments, at least one of the side-walls of at least one of the cutouts forms an angle 958 with the exterior surface 956 that is greater than 90°. In at least some embodiments, at least one of the side-walls of at least one of the cutouts forms an angle with the exterior surface 956 that is at least 90°, 100°, 110°, 120°, 130°, 140°, 150°, or more.

Figure 9D:
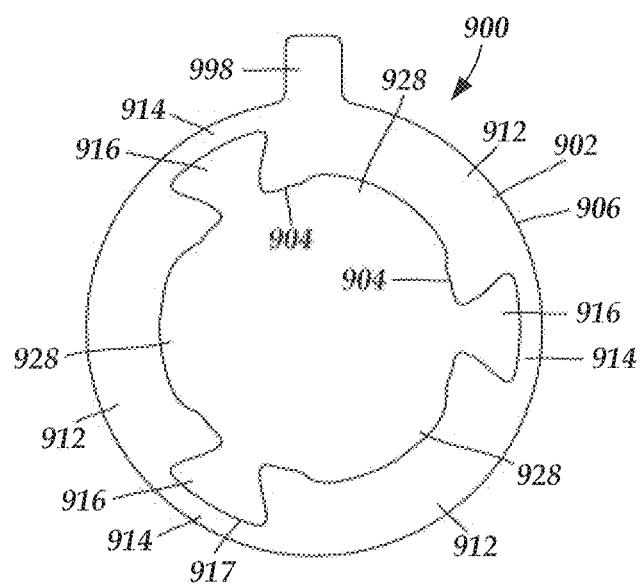
FIG. 9D is a schematic transverse cross-sectional view of one embodiment of the pre-electrode of FIG. 9A with an alignment tab disposed along an outer surface of the pre-electrode, according to the invention.

In at least some embodiments the pre-electrode includes an alignment feature formed as one or more alignment tabs. FIG. 9D illustrates, in transverse cross section, an alignment tab 998 extending radially outward from the outer surface 906 of the body 902. In some embodiments, the one or more alignment tabs extend along an entire length of the pre-electrode from the proximal end to the distal end. In other embodiments, the one or more alignment tabs extend less than the entire length of the pre-electrode from the proximal end to the distal end.

As with the alignment slits and alignment apertures, the alignment tabs may be used (either alternately or addition to an alignment slit or one or more alignment apertures) to mark the exterior surface of the pre-electrode to indicate the position of a segmented electrode beneath to facilitate manufacture and orientation of the pre-electrode in the desired position during manufacture. Such alignment tabs may facilitate aligning several pre-electrodes so that the underlying segmented electrodes will have the proper relative positions after completion of the manufacture of the lead. In at least some embodiments, the alignment tabs 998 do not extend into the segmented electrode 912, so that when the connecting material 914 of the pre-electrode 900 is removed by, for example, grinding, to release the individual segmented electrodes, the alignment tab 998 is also removed.

Figure 10A:
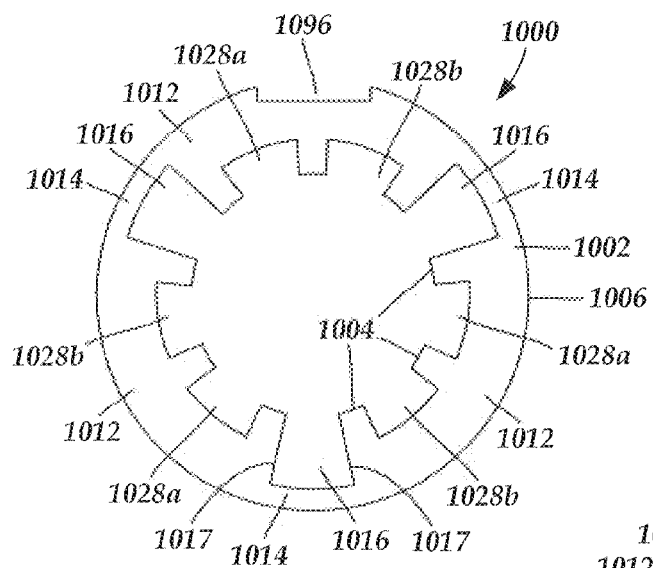
FIG. 10A is a schematic transverse cross-sectional view of a fifth embodiment of a pre-electrode having multiple channels and an alignment groove formed along an outer surface of the pre-electrode, according to the invention.
Figure 10B:
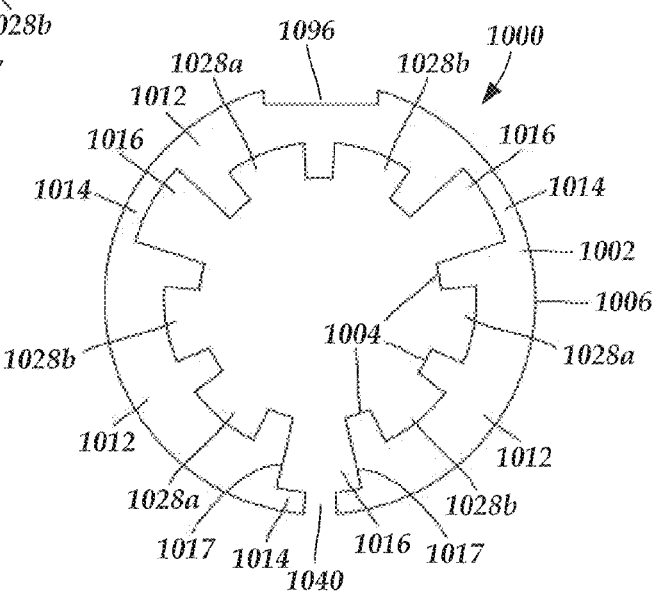
FIG. 10B is a schematic transverse cross-sectional view of one embodiment of the pre-electrode of FIG. 10A with an alignment slit defined along a cutout of the pre-electrode and an alignment groove formed along an outer surface of the pre-electrode, according to the invention.
Figure 10C:
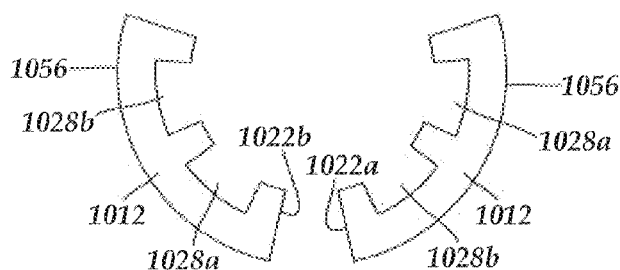
FIG. 10C is a schematic transverse cross-sectional view of one embodiment of a set of segmented electrodes formed by removing connecting material of the pre-electrode of FIG. 10A or FIG. 10B, according to the invention.

Turning to FIGS. 10A-10C, in at least some embodiments the pre-electrode includes an alignment feature formed as at least one alignment groove. In at least some embodiments, the pre-electrode is configured and arranged such that each of the segmented electrodes defines multiple channels. FIGS. 10A-10B illustrate schematic transverse cross-sectional views of pre-electrode 1000. The pre-electrode 1000 includes a body 1002 that has an interior surface 1004, an outer surface 1006, and that defines cutouts 1016.

The cutouts 1016 have perimeters 1017 extending between adjacent portions of the interior surface 1004 of the pre-electrode 1000. Each cutout abuts two segmented electrodes with portions of the perimeter 1017 forming side-walls of those segmented electrodes. The cutouts 1016 are defined between the individual segmented electrodes and typically define the spacing between the segmented electrodes. The pre-electrode 1000 includes individual segmented electrodes 1012 joined by connecting material 1014 that can be removed (for example, by grinding, machining, etching, ablating, or otherwise removing the connecting material 1014) to leave the separated segmented electrodes 1012 when the pre-electrode is in place on the lead.

In FIG. 10A, the body 1002 of the pre-electrode 1000 has a closed-loop transverse circumference. In FIG. 10B, the body 1002 defines an alignment slit 1040. The alignment slit 1040 is disposed along one of the cutouts 1016 and extends along the entire length of the cutout 1016 between a proximal end and a distal end of the body 1002, effectively making the body 1002 of the pre-electrode 1000 open-loop, or C-shaped (i.e., the cross-sectional circumference, or outer surface 1006, of the pre-electrode is discontinuous).

In at least some embodiments, the alignment slit 1040 is entirely disposed along one of the cutouts 1016. In which case, when the connecting material 1014 of the pre-electrode 1000 is removed the alignment slit 1040 may be at least partially disposed within the spacing between two segmented electrodes of the set of segmented electrodes formed along the pre-electrode 1000. In at least some embodiments, when the connecting material 1014 of the pre-electrode 1000 is removed the alignment slit 1040 is entirely disposed within the spacing between two segmented electrodes of the set of segmented electrodes formed along the pre-electrode 1000. In at least some embodiments, the alignment slit 1040 is positioned such that removal of the connecting material 1014 causes a corresponding removal of the alignment slit 1040 without affecting the shape of any of the formed segmented electrodes.

The pre-electrode 1000 defines one or more alignment grooves 1096 formed on the outer surface 1006 of the pre-electrode. As with the alignment slits, alignment apertures, and alignment tabs, the alignment grooves 1020 may be used (either alternately or addition to an alignment slit, one or more alignment apertures, or one or more alignment tabs) to mark the exterior surface of the pre-electrode to indicate the position of a segmented electrode beneath to facilitate manufacture and orientation, of the pre-electrode in the desired position during manufacture. Such alignment grooves 1096 may facilitate aligning several pre-electrodes so that the underlying segmented electrodes will have the proper relative positions after completion of the manufacture of the lead.

In some embodiments, the alignment grooves 1096 do not extend into the segmented electrode 1012, so that when the connecting material 1014 of the pre-electrode 1000 is removed by, for example, grinding, to release the individual segmented electrodes, the alignment grooves 1096 is no longer visible. In other embodiments, the alignment grooves 1096 do extend into the segmented electrode 1012 and may be used to mark the segmented electrode.

FIG. 10C illustrates, in transverse cross section, the set of segmented electrodes 1012 formed after removal of the connecting material 1014 of the pre-electrode 1000. The segmented electrodes 1012 include the interior surface 1004, and exterior surface 1056, and opposing side-walls 1022a and 1022b extending radially between the interior surface 1004 and the exterior surface 1056. It will be understood that, although not shown in FIG. 10C, the segmented electrodes 1012 also include a proximal end and an opposing distal end. These proximal and distal ends are typically the same proximal and distal ends as that of the pre-electrode along which the segmented are disposed (see e.g., FIG. 6B).

The interior surfaces 1004 of the segmented electrodes 1012 are typically the same surfaces as the interior surface 1004 of the pre-electrode 1000. The opposing side-walls 1022a and 1022b are typically defined by portions of the perimeters 1017 of the cutouts 1016. In at least some embodiments, when removing the connecting material 1014, portions of the perimeter 1017 of the cutouts 1016 (particularly the lateral-most portions of the perimeter 1017) may be removed along with the connecting material 1014. The exterior surfaces 1056 of the segmented electrodes 1012 are formed from inner portions of the body 1002 of the pre-electrode 1000 that previously abutted the connecting material 1014 prior to removal of the connecting material 1014.

The pre-electrode 1000 further includes multiple channels disposed along the interior surface 1004 of the pre-electrode 1000. In at least some embodiments, the channels are arranged such that at least two channels, such as channels 1028a and 1028b, are formed along the interior surfaces 1004 of at least one of the segmented electrodes 1012. In FIG. 10C, two channels are shown defined along the interior surface 1004 of each of the segmented electrodes 1012. In other embodiments, more than two channels are defined along the interior surface 1004 of each segmented electrode 1012. In at least some embodiments, the two or more channels have the same size, or shape, or both. In other embodiments, the two or more channels have different sizes, or shapes, or both from one another.

It will be understood that features from any of the pre-electrodes 600, 700, 800, 900, and 1000 are combinable and may be used interchangeably with one another. For example, the cutouts of any of the pre-electrodes 600, 700, 800, 900, and 1000 may be used with the channels of any of the pre-electrodes 600, 800, 900, and 1000. Additionally, the alignment features, such as the alignment apertures, the alignment slits, alignment tabs, and the alignment grooves may be used in any combination with each other and with any of the pre-electrodes 600, 700, 800, 900, and 1000.

The above specification, examples, and data provide a description of the manufacture and use of the composition of the invention. Since many embodiments of the invention can be made without departing from, the spirit and scope of the invention, the invention also resides in the claims hereinafter appended.

What is claimed as new and desired to be protected by Letters Patent of the United States is:

1. A stimulation lead, comprising:
   a lead body comprising a longitudinal surface, a distal end portion, a proximal end portion, and a longitudinal length;
   a plurality of terminals disposed along the proximal end portion of the lead body;
   a plurality of electrodes disposed along the distal end portion of the lead body, the plurality of electrodes comprising a plurality of segmented electrodes, each of the plurality of segmented electrodes comprising a proximal end, a distal end, an exterior surface, an interior surface opposite the exterior surface, a first side-wall extending radially between the interior surface and the exterior surface from the distal end to the proximal end, a second side-wall opposite to the first side-wall and extending radially between interior surface and the exterior surface from the distal end to the proximal end, at least one of the plurality of segmented electrodes defining at least one open cavity formed along the first side-wall of the segmented electrode and extending circumferentially inwardly and extending from the distal end to the proximal end, the at least one open cavity configured and arranged to facilitate adhesion of the segmented electrode to the lead body; and
   a plurality of conductors electrically coupling the plurality of terminals to the plurality of electrodes.

2. The stimulation lead of claim 1, wherein the at least one open cavity comprises and internal ridge that extends from the distal end to the proximal end of the at least one segmented electrode.

3. The stimulation lead of claim 1, wherein the at least one open cavity receives a portion of at least one conductor of the plurality of conductors.

4. The stimulation lead of claim 1, wherein the at least one open cavity receives a portion or at least one conductor of the plurality of conductors.

5. The stimulation lead of claim 1, wherein at least one of the plurality of segmented electrodes receives a portion of, and electrically couples to, at least two conductors of the plurality of conductors.

6. The stimulation lead of claim 1, wherein the first side-wall and the exterior surface of at least one of the plurality of segmented electrodes form an angle that is greater than 90°.

7. The stimulation lead of claim 1, wherein at least one of the plurality of segmented electrodes further defines at least one channel formed along the interior surface of the segmented electrode and extending from the proximal end to the distal end of the segmented electrode, the at least one channel configured and arranged to facilitate adhesion of the segmented electrode to the lead body.

8. The stimulation lead of claim 7, wherein the at least one channel has an arcuate cross-sectional profile.

9. The stimulation lead of claim 7, wherein the at least one channel has a U-shaped cross-sectional profile.

10. The stimulation lead of claim 7, wherein the at least one channel extends along at least 30% of a circumferential length of the interior surface of the segmented electrode.

11. A method of making a stimulation lead, the method comprising
    disposing at least one pre-electrode along a distal end portion of a lead body, the at least one pre-electrode comprising a substantially-cylindrical body comprising an outer surface, an interior surface opposite the outer surface, a proximal end, and a distal end, the body comprising
        a plurality of segmented electrodes disposed along the body in a spaced-apart configuration, each of the plurality of segmented electrodes extending between the proximal end and the distal end of the body, each of the plurality of segmented electrodes also extending between the interior surface of the body and an exterior surface, each of the plurality of segmented electrodes comprising a first side-wall and a second side-wall opposite to the first side-wall, the first side-wall and the second side-wall each extending radially between the interior surface and the exterior surface from the distal end to the proximal end, the plurality of segmented electrodes comprising a first segmented electrode and a second segmented electrode, the first segmented electrode defining a first open cavity extending circumferentially inwardly into the first side-wall from the distal end to the proximal end,
        connecting material coupling the first segmented electrode to the second segmented electrode, and
        a cutout defined along the body between the first segmented electrode and the second segmented electrode; and
    placing non-conductive material within the first open cavity to facilitate retention of the first segmented electrode with the lead body.

12. The method of claim 11, further comprising placing non-conductive material within at least one channel formed along the interior surface of the first segmented electrode, the at least one channel extending from the distal end to the proximal end.

13. The method of claim 11, further comprising removing the connecting material to physically separate the first segmented electrode from the second segmented electrode.

14. The method of claim 11, wherein the at least one pre-electrode comprises a first pre-electrode and a second pre-electrode, and further comprising circumferentially aligning the plurality of segmented electrodes of the first pre-electrode with the plurality of segmented electrodes of the second pre-electrode along a longitudinal length of the lead body.

15. The method of claim 11, further comprising receiving within the at least one open cavity a portion of at least one conductor extending along a longitudinal length of the lead body.

16. A pre-electrode for a stimulation lead, the pre-electrode comprising:
    a substantially-cylindrical body comprising an outer surface, an interior surface opposite the outer surface, a proximal end, and a distal end;
    a plurality of segmented electrodes disposed along the body in a spaced-apart configuration, each of the plurality of segmented electrodes having opposing side-walls extending between the proximal end and the distal end of the body;
    at least one open cavity defined along at least one side-wall of at least one of the plurality of segmented electrodes, the at least one open cavity extending between the proximal end and the distal end of the body;
    connecting material disposed along the outer surface of the body, the connecting material coupling each of the plurality of segmented electrodes to one another;
    a plurality of cutouts defined between adjacent segmented electrodes of the plurality of segmented electrodes; and
    at least one alignment feature formed on or in the outer surface of the body.

17. The pre-electrode of claim 16, wherein the at least one alignment feature forms an opening extending between the outer surface of the body and one of the plurality of cutouts.

18. The pre-electrode of claim 17, wherein the at least one alignment feature comprises an alignment slit extending between the proximal end of the body to the distal end of the body.

19. The pre-electrode of claim 17, wherein the at least one alignment feature comprises at least one of an alignment aperture extending less than an entire dimension between the proximal end of the body to the distal end of the body.

20. The pre-electrode of claim 16, wherein the at least one alignment feature comprises at least one of an alignment tab extending radially outward from the outer surface of the body.

* * * * *